United States Patent [19]

Hanifin et al.

[11] 4,189,436

[45] Feb. 19, 1980

[54] β-OXO-3-THIOPHENE PROPIONITRILE AND β-AMINO-2-(3)-THIOPHENE ACRYLONITRILES

[75] Inventors: John W. Hanifin, Suffern; David N. Ridge, Upper Grandview, both of N.Y.

[73] Assignee: American Cyanamid Company, Stamford, Conn.

[21] Appl. No.: 936,443

[22] Filed: Aug. 24, 1978

Related U.S. Application Data

[63] Continuation-in-part of Ser. No. 853,980, Nov. 22, 1977, abandoned.

[51] Int. Cl.$^2$ ................. C07D 333/16; C07D 333/00; A01N 9/00
[52] U.S. Cl. ...................................... 549/72; 424/275; 549/74

[58] Field of Search ................ 260/329 AM, 332.3 C; 424/275

[56] References Cited

U.S. PATENT DOCUMENTS 2,540,982  2/1951  Emerson et al. ..................... 260/329

*Primary Examiner*—Alan Siegel
*Attorney, Agent, or Firm*—Edward A. Conroy, Jr.

[57] ABSTRACT

This disclosure describes new compounds and compositions of matter useful as anti-inflammatory agents and as inhibitors of the progressive joint deterioration characteristic of arthritic disease and the methods of meliorating inflammation and of inhibiting joint deterioration in mammals therewith, the active ingredients of said compositions of matter being β-oxo-3-thiophenepropionitrile, β-amino-2-thiopheneacrylonitrile, and/or β-amino-3-thiopheneacrylonitrile.

3 Claims, No Drawings

β-OXO-3-THIOPHENE PROPIONITRILE AND β-AMINO-2-(3)-THIOPHENE ACRYLONITRILES

CROSS REFERENCE TO RELATED APPLICATION

This application is a continuation-in-part of our co-pending application Ser. No. 853,980, filed November 22, 1977, now abandoned.

BRIEF SUMMARY OF THE INVENTION

This invention is concerned with the following new compounds:

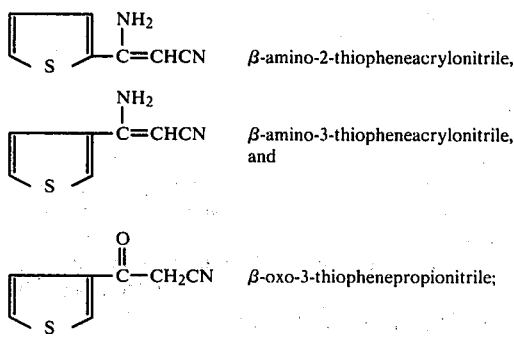

β-amino-2-thiopheneacrylonitrile,

β-amino-3-thiopheneacrylonitrile, and

β-oxo-3-thiophenepropionitrile;

and with novel compositions of matter containing them useful as anti-inflammatory agents and as inhibitors of the progressive joint deterioration characteristic of arthritic disease. The invention includes the new compositions of matter and the methods of meliorating inflammation and of inhibiting joint deterioration in mammals therewith.

DETAILED DESCRIPTION OF THE INVENTION

The invention also includes the cationic salts of β-oxo-3-thiophenepropionitrile with pharmacologically acceptable metal cations, ammonium, amine cations, or quaternary ammonium cations. Preferred metal cations are those derived from the alkali metals, e.g. lithium, sodium and potassium, and from the alkaline earth metals, e.g. magnesium and calcium, although cationic forms of other metals, e.g. aluminum, zinc, iron and in particular copper, are within the scope of the invention.

Pharmacologically acceptable amine cations and those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and aryliphatic amines containing up to and including 18 carbon atoms, as well as heterocyclic amines, e.g. piperidine, morpholine, pyrrolidine, piperazine and lower alkyl derivative thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxy-methyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like. Examples of suitable pharmacologically acceptable quaternary ammonium cations are tetramethylammonium, tetraethylammonium, benzyltrimethylammonium, phenyltriethylammonium and the like.

The compounds of the present invention have been found to be highly useful for meliorating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gm. to about 7.0 gm. of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chloro-phenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg./ml. of the finished compositions. These active compounds are equally adapted to intravenous administration when diluted with water or diluents employed in intravenous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

Adjuvant induced experimental polyarthritis is a specific systemic disease of the rat which shares interesting similarities with rheumatoid arthritis. Specifically, the histology of the two diseases bears a remarkable resemblance as shown by C. M. Pearson et al., Am. J. Pathol. 42, 73 (1963). E. M. Glenn, Am. J. Vet. Res. 27 (116) 339 (1966) has classified adjuvant induced polyarthritis as a crippling and permanent deformity resulting from diffuse connective tissue involvement around certain susceptible joints in the rat. Zahiri et al., Can. Med. Ass. J. 101, 269 (1969) have shown that the fusiform swelling of the distal joints is associated with edema, congestion and synovitis including pannus formation, all of which precede the ultimate destruction of bone and cartilage. Furthermore, Zahiri et al. indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration. See S. Wong et al., J. Pharm. & Exptl. Ther. 185, 127 (1973) and G. R. Bobalick et al., Agents & Actions 4, 364 (1974). In a similar manner, inhibition of the progress of arthritis in paws of rats treated with the compounds of this invention also lessens associated joint deterioration.

The following test shows the activity of the compounds of this invention against chronic inflammation in adjuvant induced arthritis which is accompanied by joint destruction. Groups of three Royal Hart, Wistar strain rats weighing $200 \pm 10$ grams each were injected intradermally in the right hind paw with Freund's adjuvant (dried human tubercle bacilli in a mineral oil vehicle) at a dose of 2 mg./kg. of body weight. Test compounds were administered orally in a 1.5% starch vehicle at various doses once daily on days 0 through 13 post challenge. Control rats were treated in a similar manner, but given only starch vehicle. On the 14th and 21st day post challenge the diameter of the injected paw (primary lesion) was measured by micrometer caliper. The volume of inflamed paws were estimated from these measurements and the results are expressed as percent inhibition of swelling as compared to controls. At the same time, the other inflamed sites, such as ears, paws and tail (secondary lesions) were observed and each rat was graded as to degree of inflammation and swelling present. The grading is based on a scale of 0 to 24, where 0 represents a complete absence of induced arthritic nodules and 24 represents the maximum degree of inflammation. The mean grade for each treated group is calculated and the effects of each compound are expressed as percent inhibition of the control grade. Table I below records the results of tests conducted with the compounds of this invention and known anti-inflammatory agents. The compounds of this invention appear to suppress the progression of the arthritis and associated joint deterioration.

TABLE I

The Effect of Anti-inflammatory Agents on Adjuvant Arthritis in Rats

| Compound | Oral Dose mg./kg. of Body Weight | Dead/Treated at 21 Days | Mean Weight Gain (grams) | | % Inhibition of Swelling (primary lesion) | | % Inhibition of Control Grade (secondary lesion) | |
|---|---|---|---|---|---|---|---|---|
| | | | Day 14 | Day 21 | Day 14 | Day 21 | Day 14 | Day 21 |
| Normal rats | — | 8/186 | 77 | 112 | — | — | — | — |
| Adjuvant controls | — | 56/630 | 36 | 31 | 0 | 0 | 0 | 0 |
| Indomethocin | 2 | 8/57 | 68 | 68 | 51 | 24 | 38 | 25 |
| | 1 | 9/54 | 63 | 65 | 46 | 19 | 34 | 20 |
| | 0.5 | 5/54 | 53 | 51 | 40 | 20 | 25 | 17 |
| | 0.25 | 0/9 | 51 | 57 | 30 | 4 | 22 | 4 |
| Aspirin | 400 | 18/57 | 41 | 55 | 73 | 48 | 58 | 45 |
| | 200 | 10/66 | 40 | 44 | 48 | 27 | 26 | 17 |
| | 100 | 18/63 | 48 | 53 | 36 | 13 | 19 | 8 |
| | 50 | 2/21 | 56 | 44 | 23 | 3 | 12 | 9 |
| Phenylbutazone | 150 | 2/27 | 40 | 50 | 75 | 44 | 54 | 31 |
| | 75 | 2/39 | 51 | 50 | 62 | 28 | 27 | 15 |
| | 37.5 | 5/39 | 53 | 53 | 56 | 14 | 18 | 13 |
| | 18.8 | 2/21 | 50 | 45 | 31 | 7 | 4 | 8 |

TABLE I-continued

The Effect of Anti-inflammatory Agents on Adjuvant Arthritis in Rats

| Compound | Oral Dose mg./kg. of Body Weight | Dead/Treated at 21 Days | Mean Weight Gain (grams) | | % Inhibition of Swelling (primary lesion) | | % Inhibition of Control Grade (secondary lesion) | |
|---|---|---|---|---|---|---|---|---|
| | | | Day 14 | Day 21 | Day 14 | Day 21 | Day 14 | Day 21 |
| β-Amino-2-thiophene-acrylonitrile | 200 | 6/18 | 36 | 53 | 70 | 61 | 80 | 57 |
| | 100 | 2/18 | 45 | 51 | 49 | 27 | 25 | 16 |
| | 50 | 1/33 | 54 | 50 | 44 | 23 | 21 | 6 |
| β-Amino-3-thiophene-acrylonitrile | 50 | 2/18 | 47 | 54 | 52 | 41 | — | — |
| β-Oxo-3-thiophene-propionitrile | 50 | 1/18 | 53 | 50 | 61 | 26 | — | — |

The invention will be described in greater detail in conjunction with the following specific examples.

EXAMPLE 1

Preparation of β-amino-2-thiopheneacrylonitrile

A reaction flask is dried by flaming with a stream of nitrogen passing through it. About 100 ml. of ammonia is condensed in the reaction flask and a small piece of sodium is added, giving a blue color. The color is discharged with ferric chloride and 2.7 g. of sodium is added. When the blue color disappears, 4.91 ml. of acetonitrile in 10 ml. of diethyl ether is added. The reaction is cooled in a dry ice-acetone bath and 9.28 g. of 2-thiophenecarbonitrile in 25 ml. of tetrahydrofuran is added dropwise. Cooling is continued for 30 minutes then the ammonia and solvent are allowed to evaporate. A 50 ml. portion of water is added and the mixture is extracted with methylene chloride. The methylene chloride extracts are dried over sodium sulfate and then passed through Magnesol ®. Hexanes are added and the filtrate is evaporated on a steam bath to an oil. This oil is dry column chromatographed on silica gel, eluting with methylene chloride. The fraction containing the desired product is taken up in methylene chloride, passed through Magnesol ® and the filtrate is evaporated on a steam bath with the addition of hexanes until an oil comes out. Cooling and seeding gives the desired product as crystals, m.p. 50°–54° C.

EXAMPLE 2

Preparation of β-amino-3-thiopheneacrylonitrile

A 500 ml. three necked flask is equipped with a mechanical stirrer, gas inlet, dry ice condenser, potassium hydroxide drying tube, and addition funnel. A 100 ml. portion of ammonia is condensed into the flask and a pellet of sodium is added. When the dark blue color persists, ferric chloride is added discharging the color to brown. A 3.2 g. portion of sodium is added and the mixture is allowed to stand for 45 minutes. A 5.7 ml. portion of acetonitrile in 10 ml. of tetrahydrofuran is added and the reaction is stirred for 20 minutes. The reaction is cooled in a dry ice-acetone bath and 10.9 g. of 3-thiophenecarbonitrile in 25 ml. of tetrahydrofuran is added. The reaction is stirred in the cold bath for 90 minutes, then at reflux for 3 hours. A 7.4 g. portion of ammonium chloride is added and the mixture is allowed to evaporate overnight. A 100 ml. portion of water and 100 ml. of chloroform are added and the mixture is filtered. The aqueous phase is extracted with chloroform, the combined organic solution is washed once with water, dried over magnesium sulfate and filtered through Magnesol ®. The filtrate is evaporated in vacuo to an orange oil. A 30 ml. portion of benzene is added and then petroleum ether until the mixture is cloudy. Cooling produces a precipitate which is collected and recrystallized from benzene giving the desired product as a solid, m.p. 67°–69.5° C.

EXAMPLE 3

Preparation of β-oxo-3-thiophenepropionitrile

A 1.2 g. portion of β-amino-3-thiopheneacrylonitrile is added to 10 ml. of 1 N hydrochloric acid. A 40 ml. portion of methanol is added and the mixture is stirred for 3 hours. The mixture is evaporated in vacuo to a residue which is dissolved in 35 ml. of hot methanol and treated with charcoal. After cooling, petroleum ether is added, the mixture is filtered and the solid collected is discarded. The filtrate is allowed to evaporate and the residue is dissolved in 35 ml. of hot isopropanol and isoluble material filtered and discarded. The filtrate is cooled and the solid is collected giving the desired product as white plates, m.p. 87°–88° C.

EXAMPLE 4

Preparation of Parenteral Solution

In a solution of 700 ml. of propylene glycol and 200 ml. of water for injection is suspended 20.0 grams of β-oxo-3-thiophenepropionitrile, sodium salt with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 5

Preparation of Topical Cream

| Ingredient | Amount |
|---|---|
| β-oxo-3-thiophenepropionitrile | 1.0% |
| Ethoxylated stearyl alcohol | 10.0% |
| Benzyl alcohol | 0.9% |
| Isopropyl palmitate | 5.0% |
| Glycerin | 5.0% |
| Sorbitol solution (USP) | 5.0% |
| Lactic acid qs to pH 4.0–5.0 | |
| Water qs ad | 100.0% |

The ethoxylated stearyl alcohol and isopropyl palmitate are heated to liquifying temperature. About 95% of the total volume of water is placed in a separate container followed by the glycerin and sorbitol solution. This aqueous mixture is brought to a boil and then cooled to 60°–75° C. The β-oxo-3-thiophenepropionitrile is added to the wax phase and the mixture is stirred until a clear solution is obtained. The benzyl alcohol is added and dissolved in the wax phase. The water phase is passed through a screen into the wax phase while maintaining agitation. Both phases are kept at about the same temperature during transfer. The mixture is cooled while agitation is continued. At a temperature of 50°–55° C. the balance of the water is added. The pH is adjusted to 4.0–5.0 with lactic acid. The batch is cooled with minimum agitation until the cream sets in its final form.

EXAMPLE 6

Preparation of 50 mg. Tablets

| Per Tablet | | Per 10,000 Tablets |
|---|---|---|
| 0.050 gm. | β-amino-2-thiopheneacrylonitrile | 500 gm. |
| 0.080 gm. | Lactose | 800 gm. |
| 0.010 gm. | Corn starch (for mix) | 100 gm. |
| 0.008 gm. | Corn starch (for paste) | 75 gm. |
| 0.148 gm. | | 1475 gm. |
| 0.002 gm. | Magnesium stearate (1%) | 15 gm. |
| 0.150 gm. | | 1490 gm. |

The β-amino-2-thiopheneacrylonitrile, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 7

Preparation of Oral Suspension

| Ingredient | Amount |
|---|---|
| β-amino-3-thiopheneacrylonitrile | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs ad | 100 ml. |

The sorbitol solution is added to 40 ml. of distilled water and the β-amino-3-thiopheneacrylonitrile is suspended therein. The saccharin, sodium benzoate, flavor and dye are added and dissolved. The volume is adjusted to 100 ml. with distilled water. Each ml. of syrup contains 5 mg. of active component.

We claim:
1. β-Amino-2-thiopheneacrylonitrile.
2. β-Amino-3-thiopheneacrylonitrile.
3. A compound selected from the group consisting of β-oxo-3-thiophenepropionitrile and the pharmacologically acceptable cationic salts thereof.

* * * * *